United States Patent [19]

Nagase et al.

[11] Patent Number: 5,200,488

[45] Date of Patent: Apr. 6, 1993

[54] POLYORGANOSILOXANE HAVING A QUATERNARY SALT AT ITS ONE TERMINAL AND PERCUTANEOUS ABSORPTION-PROMOTING AGENT

[75] Inventors: Yu Nagase; Takao Aoyagi, both of Sagamihara; Tomoko Nakamura, Ayase, all of Japan

[73] Assignee: Sagami Chemical Research Center, Tokyo, Japan

[21] Appl. No.: 787,103

[22] Filed: Nov. 4, 1991

[30] Foreign Application Priority Data

Nov. 6, 1990 [JP] Japan .................... 2-298938
May 8, 1991 [JP] Japan .................... 3-131597

[51] Int. Cl.$^5$ ............................................. C08G 77/04
[52] U.S. Cl. ............................. 528/28; 556/425; 546/14
[58] Field of Search ................. 556/425; 528/28; 546/14

[56] References Cited

U.S. PATENT DOCUMENTS 4,093,642  6/1978  Schilling et al. ............ 556/425
4,472,566  9/1984  Ziemelis et al. ............ 556/425
5,041,590  8/1991  Snow ........................... 556/425

Primary Examiner—Melvyn I. Marquis
Attorney, Agent, or Firm—Oblon, Spivak, McClelland, Maier & Neustadt

[57] ABSTRACT

A polyorganosiloxane having a quaternary salt at its one terminal, of the following formula (I):

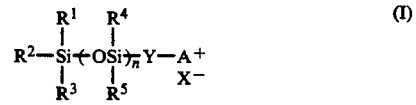

wherein A is

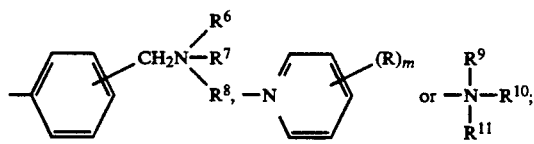

$X^-$ is a counter anion in the quaternary salt; each of $R^1$ to $R^5$ which may be the same or different, is an alkyl group, a substituted alkyl group or a phenyl group; Y is a $C_{1-6}$ linear or branched bivalent alkylene or oxyalkylene group; and n is an integer of at least 1, provided that when n is 2 or more, each of $R^4$ and $R^5$ may be the same or different, wherein each of $R^6$ to $R^8$ which may be the same or different, is an alkyl group, a substituted alkyl group or a phenyl group, or $R^6$ to $R^8$ together form a ring and/or an unsaturated bond; R is a $C_{1-6}$ alkyl group or a phenyl group; m is an integer of from 0 to 3, provided that when m is 2 or 3, R may be the same of different; and each of $R^9$ to $R^{11}$ which may be the same or different, is a phenyl group, a benzyl group or a $C_{1-6}$ alkyl group.

Such polyorganosiloxane is useful for promoting percutaneous absorption of a drug.

4 Claims, No Drawings

POLYORGANOSILOXANE HAVING A QUATERNARY SALT AT ITS ONE TERMINAL AND PERCUTANEOUS ABSORPTION-PROMOTING AGENT

The present invention relates to a novel polyorganosiloxane having a quaternary salt at its one terminal and its use as a percutaneous absorption-promoting agent which promotes the penetration and absorption of a drug through the skin.

Studies have been actively conducted on drug delivery systems (DDS) for the purpose of efficiently delivering drugs to desired sites and avoiding side effects. Among them, a percutaneous absorption system wherein the skin is the application site of a drug, has attracted an attention in recent years. The merits of this system include ① it is thereby possible to avoid the first-pass effect at the liver, ② the percutaneous penetration rate of the drug can be controlled so that a long active constant drug level can be maintained, ③ the administration is not influenced by foods or vomiting, ④ the administration can easily be adjusted, and ⑤ the drug can be administered in the vicinity of the desired site. However, it still has drawbacks such that ① the application is limited to a drug, the dose of which is relatively small, ② useful drugs are relatively limited, ③ there is a possibility that deterioration of the keratin layer or a skin allergy reaction is thereby promoted, and ④ no rapid action can be expected. Under these circumstances, a combined use of a percutaneous absorption-promoting agent is being studied to overcome such drawbacks.

Heretofore, it has been proposed to use, for example, dimethylsulfoxide, 1-dodecyl-2-pyrrolidone, 1-dodecylazacycloheptan-2-one or urea ("Drug Delivery System" compiled by Kaoru Kaetsu, p 213–237, CMC). The present inventors have previously proposed, as percutaneous absorption-promoting agents having low toxicity and irritation to the skin, polymer compounds such as a polymer having a benzalkonium salt on its side chain (Japanese Unexamined Patent Publication No. 131127/1989), a polymer having a pyridinium salt on its side chain and a polyorganosiloxane having an N-methylpyridinium salt at its one terminal (collection of preparatory papers for delivery at the 59th Spring Annual Meeting of Japan Chemical Society, p 993, 1990).

However, among the above promoting agents, particularly low molecular weight compounds such as dimethylsulfoxide, 1-dodecyl-2-pyrrolidone, 1-dodecylazacycloheptan-2-one and urea, had problems in practical application in that they have a toxicity or irritation to the skin. On the other hand, the above polymer compounds proposed by the present inventors all have excellent promoting effects, and they have at the same time low toxicity and low irritation to the skin, since as being polymers, they do not penetrate into the interior of the skin. Especially, the polyorganosiloxane having an N-methylpyridinium salt at its one terminal is composed of a polysiloxane chain which is inactive to the vital body, and thus its toxicity is very low. However, these conventional polysiloxane promoting agents have a problem that the synthesis of the starting compounds is cumbersome and problematic when the synthesis is to be practically carried out for mass production.

The present inventors have made extensive research efforts to solve the above problem. As a result, they have found that a polyorganosiloxane having a halogenated methylphenyl or alkyl group at its one terminal can readily be obtained and further that a polyorganosiloxane having a quaternary salt at its one terminal which can readily be prepared therefrom, exhibits excellent percutaneous absorption promoting effects. The present invention has been accomplished on the basis of these discoveries.

Thus, the present invention provides a polyorganosiloxane having a quaternary salt at its one terminal, of the following formula (I):

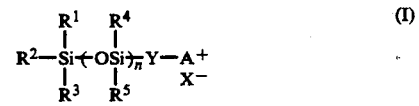

wherein A is

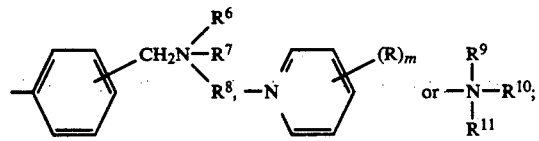

X⁻ is a counter anion in the quaternary salt; each of $R^1$ to $R^5$ which may be the same or different, is an alkyl group, a substituted alkyl group or a phenyl group; Y is a $C_{1-6}$ linear or branched bivalent alkylene or oxyalkylene group; and n is an integer of at least 1, provided that when n is 2 or more, each of $R^4$ and $R^5$ may be the same or different, wherein each of $R^6$ to $R^8$ which may be the same or different, is an alkyl group, a substituted alkyl group or a phenyl group, or $R^6$ to $R^8$ together form a ring and/or an unsaturated bond; R is a $C_{1-6}$ alkyl group or a phenyl group; m is an integer of from 0 to 3, provided that when m is 2 or 3, each R may be the same of different; and each of $R^9$ to $R^{11}$ which may be the same or different, is a phenyl group, a benzyl group or a $C_{1-6}$ alkyl group.

The present invention also provides an agent for promoting percutaneous absorption of a drug, which consists essentially of such a polyorganosiloxane.

Now, the present invention will be described in detail with reference to the preferred embodiments.

The counter anion in the quaternary salt represented by X⁻ in the above formula (I), may be a conjugate base of a mineral acid, for example, a halogen ion such as F⁻, Cl⁻, Br⁻ or I⁻, a hydroxyl ion, a carbonate ion, a sulfate ion, a hydrogensulfate ion, a sulfite ion, a nitrate ion or a phosphate ion, or a conjugate base of an organic acid, for example, a carboxylic acid ion, a sulfonic acid ion or a phosphonic acid ion.

The polyorganosiloxane of the present invention can be prepared, for example, by the following methods.

Namely, a polyorganosiloxane having a quaternary salt at its one terminal, of the above formula (I) wherein A

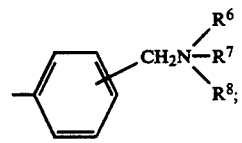

Y is a $C_{2-6}$ linear or branched bivalent alkylene or oxyalkylene group, $X^-$ is a halogen ion, and $R^1$ to $R^8$ and n are as defined above, can be produced readily and in good yield by mixing and subjecting to a quaternization reaction a polyorganosiloxane having a halogenated methylphenyl group at its one terminal, of the following formula (II):

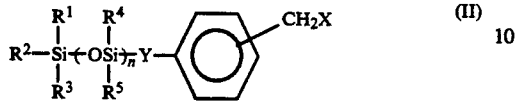

wherein X is a halogen atom, and $R^1$ to $R^5$, Y and n are as defined above, and a compound of the following formula (III):

wherein $R^6$ to $R^8$ are as defined above. Further, a polyorganosiloxane wherein $X^-$ is other than the halogen ion, can readily be obtained by ion-exchanging the halogen ion as the counter anion of the polyorganosiloxane of the formula (I) thus obtained with a conjugate base of the corresponding mineral acid or organic acid.

For the quaternization reaction, it is preferred to employ a solvent. The solvent may, for example, be hexane, benzene, toluene, diethyl ether, dioxane, tetrahydrofuran, acetone, methyl ethyl ketone, chloroform, methylene chloride, N,N-dimethylformamide, N,N-dimethylacetamide, dimethylformamide or N-methylpyrrolidone. The reaction proceeds smoothly within a range of from 0° to 100° C., preferably from 20° to 80° C.

The compound of the formula (III) to be used for the quaternization reaction, may, for example, be trimethylamine, triethylamine, tripropylamine, triisopropylamine, tributylamine, triisobutylamine, tripentylamine, trihexylamine, dimethylethylamine, dimethylpropylamine, dimethylisopropylamine, dimethylbutylamine, dimethylhexylamine, dimethyldiethylamine, N,N-dimethylaniline, N,N-diethylaniline, N,N-dipropylaniline, N,N-dibutylaniline, N,N-dipentylaniline, N,N-dihexylaniline, N-methyl-N-ethylaniline, N-methyl-N-propylaniline, N methyl-N-butylaniline, N-methyl-N-hexylaniline, N,N-dimethyl-2-naphthylamine, dimethylbenzylamine, diethylbenzylamine, N,N-dimethyle-thanolamine, 1-methylpyrrolidine, 1-methyl-3-pyrrolidinol, 1-methyl-3-pyrrolidine ethanol, 1methyl-1-methyl-2-piperidine ethanol, 4methylmorpholine, 3-methylthiazole, 1-methylindole, pyridine, α-picoline, β-picoline, γ-picoline, 3,5-dimethylpyridine, 2,4-dimethylpyridine, 2,6-dimethylpyridine, 2,4,6-trimethylpyridine, 4-ethylpyridine, 4-propylpyridine, 4-isopropylpyridine, 4-butylpyridine, 4-t-butylpyridine, 4-pentylpyridine, 4-hexylpyridine, 2-methyl-4-t-butylpyridine, 4-methyl-2,6-di-t-butylpyridine, 2-phenylpyridine, 3-phenylpyridine, 4-phenylpyridine, 4-methyl-2-phenylpyridine, 5-methyl-2phenylpyridine or 4-methyl-2,6-diphenylpyridine.

Some of the polyorganosiloxane having a halogenated methylphenyl group at its one terminal, of the above formula (II), are commercially available (such as Silaplane XN-1003, manufactured by Chisso Corporation). Those which are not commercially available, can readily be prepared as will be described, for example, in Reference Examples given hereinafter, by mixing a polyorganosiloxane having a Si—H bond at its terminal, of the following formula (IV):

wherein $R^1$ to $R^5$ are as defined above, and a compound of the following formula (V):

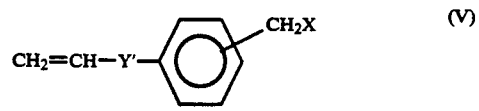

wherein X is a halogen atom, and Y' is a single bond or a $C_{1-4}$ linear or branched bivalent alkylene group or oxyalkylene group, so that the compound of the above formula (V) will be at least equimolar to the polyorganosiloxane having a Si—H bond at its one terminal, of the above formula (IV), and reacting them in the presence of a hydrosilylation catalyst.

As the hydrosilylation catalyst to be used in the above reaction, it is most common to employ a platinum-type catalyst such as platinum, platinum carbon, chloroplatinic acid or dicylopentadienylplatinum dichloride. Further, a metal complex containing palladium or rhodium is also useful. For example, $(Ph_3P)_4Pd$, $(Ph_3P)_2PdCl_2$, $(PhCN)_2PdCl_2$, $(Ph_3P)_3RhCl$, $(Ph_2PH)_2RhCl$, $(Ph_3P)_2(CO)RhCl$ or $[(C_2H_5)_3P]_2(CO)RhCl$, may be employed as the catalyst. The catalyst is used usually in an amount of from 1/100 to 1/1000 equivalent to the compound of the above formula (V). To complete this reaction, it is necessary to mix the compound of the above formula (V) in an amount of at least equimolar to the polyorganosiloxane having a Si—H bond at its one terminal, of the above formula (IV). This reaction is preferably conducted in a solvent. The solvent may, for example, be hexane, benzene, toluene, acetone, trichloroethylene, carbon tetrachloride or tetrahydrofuran. The reaction is conducted usually within a temperature range of from 40° to 100° C. and preferably conducted in an atmosphere of inert gas such as argon or nitrogen. As the compound of the above formula (V) to be used here, the following compounds may, for example, be mentioned.

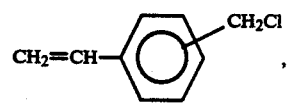

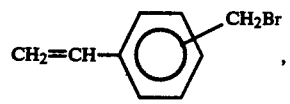

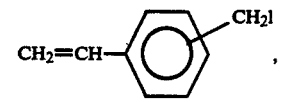

-continued

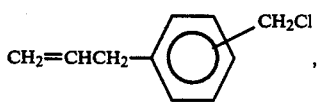,

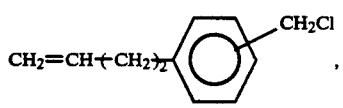,

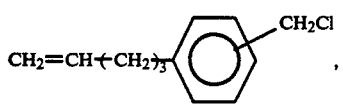,

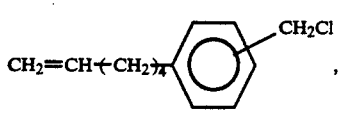,

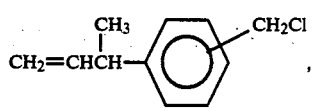,

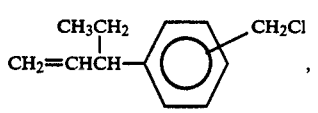,

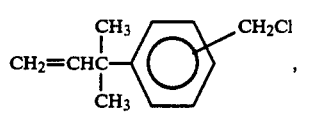,

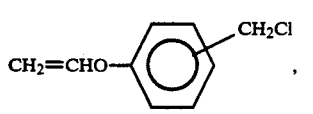,

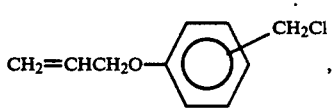,

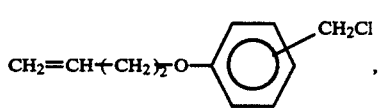,

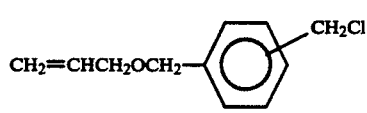

Some of the polyorganosiloxane having a Si—H bond at its one terminal, of the above formula (IV) are also commercially available (such as Silaplane FM-01 series, manufactured by Chisso Corporation). Those which are not commercially available can readily be prepared, for example, as described in Reference Examples given hereinafter, for example, by reacting a silanol compound of the following formula (VI):

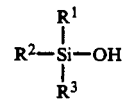 (VI)

wherein $R^1$ to $R^3$ are as defined above, with a strong base to form a silanolate anion, then reacting this anion as a initiator with a cyclosiloxane compound of the following formula (VII):

 (VII)

wherein $R^4$ and $R^5$ are as defined above, and p is an integer of from 3 to 6, and terminating the reaction by means of a chlorosilane compound of the following formula (VIII):

 (VIII)

wherein each of $R^4$ and $R^5$, which may be the same or different, is an alkyl group, a substituted alkyl group or a phenyl group.

The strong base to be used in the above reaction, may, for example, be an organic lithium compound such as methyllithium, n-butyllithium, sec-butyllithium, t-butyllithium, phenyllithium, lithiumisopropylamide or bistrimethylsilylamide, an alkali metal halide such as sodium hydride or potassium hydride, or a Grignard compound such as methylmagnesium iodide, ethylmagnesium bromide or phenylmagnesium bromide. Such a strong base is used usually in an amount of about 1 equivalent relative to the silanol compound of the above formula (VI). The reaction is preferably conducted at a relatively low temperature of from −80° C. to room temperature, so that a side reaction can be suppressed. Further, this reaction is preferably conducted in an organic solvent. The solvent to be used here, may preferably be tetrahydrofuran, benzene, toluene, hexane, chloroform or carbon tetrachloride. This reaction is preferably conducted in an atmosphere of inert gas such as argon or nitrogen.

On the other hand, a polyorganosiloxane having a Si—H bond at its one terminal, of the above formula (IV), can simply be prepared by sequentially reacting the cyclosiloxane compound of the above formula (VII) and the chlorosilane compound of the above formula (VIII) in the same manner by using as an initiator an alkyllithium compound such as methyllithium, n-butyllithium, secbutyllithium or t-butyllithium without using the silanol compound of the above formula (VI) in the above reaction. In this case, among the Substituents of $R^1$ to $R^3$ in the above formula (IV), two are the same as $R^4$ and $R^5$ in the above formula (VII) and one is the same as the alkyl group of the alkyllithium compound used here.

The silanol compound of the above formula (VI) may, for example, be trimethylsilanol, triethylsilanol, tripropylsilanol, triisopropylsilanol, tributylsilanol, tripentylsilanol, trihexylsilanol, methydiethylsilanol, dimethylethylsilanol, dimethylpropylsilanol, dimethylisopropylsilanol, dimethybutylsilanol, dimethylisobutylsilanol, dimethyl-t-butylsilanol, dimethylhexylsilanol, dimethyloctylsilanol, dimethyldecylsilanol, dimethyldodecylsilanol, dimethylhexadecylsilanol, dimethyloctadecylsilanol, dimethylphenylsilanol, methyldiphenylsilanol, triphenylsilanol, dimethylbenzylsilanol, dimethyl(2-phenylmethyl)silanol, dimethyl-3,3,3-trifluoropropylsilanol, dimethyl-1H,1H,2H,2H-pentafluorobutylsilanol, dimethyl-1H, 1H, 2H, 2H-pentafluorobutylsilanol, dimethyl-1H,1H,2H,2H-nonafluorohexylsilanol, dimethyl-1H,1H,2H,2H-tridecafluorooctylsilanol, dimethyl-1H,1H,2H,2H-heptadecafluorodecylsilanol, dimethyl-3-(1H,1Hheptafluorobutyloxy)propylsilanol, dimethyl-3-(1H,1H, 2H,2H-nonafluorohexyloxy)propylsilanol, dimethyl-3-(1H,1H,2H,2H-tridecafluorooctyloxy)-propylsilanol or dimethyl-3-1H,1H,2H,2H-pentadecafluorodecyloxy)propylsilanol.

The cyclosiloxane compound of the above formula (VII) which will be a monomer for forming a polysiloxane structure, includes, for example, the following compounds.

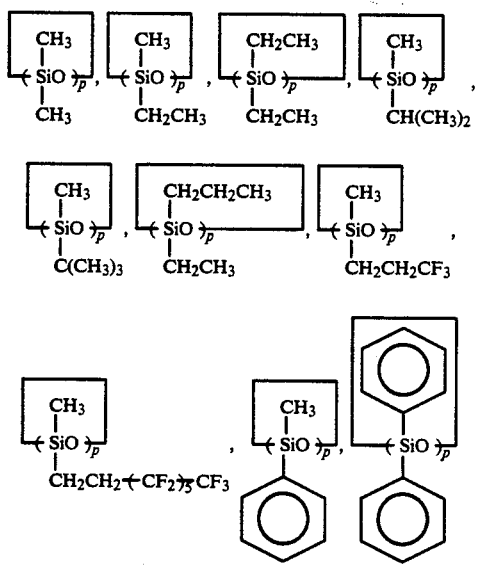

In the above formulas, p is an integer of from 3 to 6. However, from the reactivity, it is preferred to employ a cyclohexane compound of the above formula wherein p is 3. Further, such cyclohexane compounds may be used in combination as a mixture of two or more for the reaction.

The chlorosilane compound of the above formula (VIII) to be used as a terminating agent, may, for example, be dimethylchlorosilane, diethylchlorosilane, dipropylchlorosilane, dibutylchlorosilane, dihexylchlorosilane, methylethylchlorosilane, methylpropylchlorosilane, methylbutylchlorosilane, methylpentylchlorosilane, methylhexylchlorosilane, methyloxychlorosilane, methylphenylchlorosilane, diphenylchlorosilane, methyl-3,3,3-trifluoropropylchlorosilane, bis(3,3,3-trifluoropropyl)chlorosilane or methyl-1H,1H,2H,2H-tridecafluorooctylchlorosilane.

In the above-described process, it is possible to control the degree of polymerization n of the polyorganosiloxane having a Si—H bond at its one terminal, of the above formula (IV), the polyorganosiloxane having a halogenated methylphenyl group at its one terminal, of the above formula (II) or the polyorganosiloxane having a quaternary salt at its one terminal, of the above formula (I) of the present invention. On the other hand, the one wherein the degree of polymerization n is 1, can be obtained by reacting the silanol compound of the above formula (VI) with a chlorosilane compound of the above formula (VIII) directly. In order to control this degree of polymerization n to a level of at least 2, it is necessary to use the chlorohexane compound of the above formula (VII) in an amount of at least ⅓ equivalent to the initiator. In such a case, the polyorganosiloxanes of the above formulas (I), (II) and (III) will be mixtures of polyorganosiloxanes having different polymerization degrees n, whereby the measured degrees of polymerization will be average values n̄ (real number of at least 2).

The polyorganosiloxane having a quaternary salt at its one terminal, of the formula (I) wherein

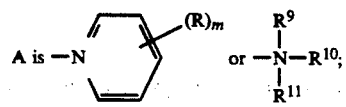

X is a halogen atom; each of $R^1$ to $R^5$ which may be the same or different, is a $C_{1-6}$ alkyl group, Y is a $C_{1-6}$ alkylene group, n is an integer of at least 3, and each of $R^4$ and $R^5$ may be the same or different; and R, m, $R^9$, $R^{10}$ and $R^{11}$ are as defined above, can be prepared by mixing and subjecting to a quaternization reaction a polyorganosiloxane having a halogenated alkyl group at its one terminal, of the formula formula (IX):

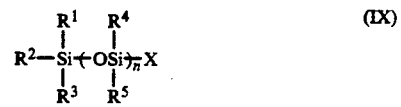

wherein X is a halogen atom and $R^1$ to $R^5$ and n are as defined above, and a pyridine derivative of the following formula (X):

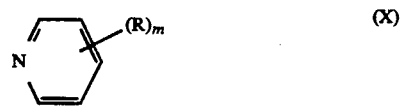

wherein R and m are as defined above, or a tertiary amine compound of the following formula (XI):

wherein $R^9$ to $R^{11}$ are as defined above. Here, the halogen atom for X in the formula (IX) is most preferably iodine, since the reaction efficiency in the above quanternization reaction can thereby be increased. However, even when X is chlorine or bromine i.e. other than iodine, it is still possible to obtain a polyorganosiloxane having a quaternary salt at its one terminal, of the above formula (I), although the yield may be low. Further, it is also possible to conduct halogen exchange in a conventional method to change the halogen to iodine and then the quaternization reaction can efficiently be conducted.

For this quaternization reaction, it is preferred to employ a solvent. The solvent may, for example, be hexane, benzene, toluene, diethyl ether, tetrahydrofuran, acetone, methyl ethyl ketone, chloroform, methylene chloride, N,N-dimethylformamide (DMF) or N-methylpyrrolidone. The reaction proceeds smoothly within a range of from 0° to 100° C., preferably from 20° to 80° C.

The pyridine derivative of the above formula (X) to be used for the quaternization reaction, may, for example, be pyridine, α-picoline, β-picoline, γ-picoline, 3,5-dimethylpyridine, 2,4-dimethylpyridine, 2,6-dimethylpyridine, 2,4,6-trimethylpyridine, 4-ethylpyridine, 4-propylpyridine, 4-isopropylpyridine, 4-butylpyridine, 4-t-butylpyridine, 4-pentylpyridine, 4-hexylpyridine, 2-methyl-4-t-butylpyridine, 4-methyl-2,6-di-t-butylpyridine, 2-phenylpyridine, 3-phenylpyridine, 4-phenylpyridine, 4-methyl-2-phenylpyridine, 5-methyl-2-phenylpyridine or 4-methyl-2,5-diphenylpyridine.

The tertiary amine compound of the above formula (XI) to be used for the quaternization reaction, may, for example, be trimethylamine, triethylamine, tripropylamine, triisopropylamine, tributylamine, triisobutylamine, tripentylamine, trihexylamine, dimethylethylamine, dimethylpropylamine, dimethylisopropylamine, dimethylbutylamine, dimethylhexylamine, methyldiethylamine, N,N-dimethylaniline, N,N-diethylaniline, N,N-dipropylaniline, N,N-dibutylaniline, N,N-dipentylaniline, N,N-dihexylaniline, N-methyl-N-ethylaniline, N-methyl-N-propylaniline, N-methyl-N-butylaniline, N-methyl-N-hexylaniline, dimethylbenzylamine or diethylbenzylamine.

The polyorganosiloxane having the halogenated alkyl group at its one terminal, of the above formula (IX) can readily be prepared, for example, by reacting a silanol compound of the following formula (XII):

wherein each of $R^1$ to $R^3$ which may be the same or different, is a $C_{1-6}$ alkyl group, with a strong base to form a silanolate anion, then reacting the silanolate anion as a initiator, with a cyclosiloxane compound of the following formula (XIII):

wherein each of $R^4$ and $R^5$ which may be the same or different, is a $C_{1-6}$ alkyl group, and p is an integer of from 3 to 6, and terminating the reaction by means of a chlorosilane compound of the following formula (XIV):

wherein X is a halogen atom, Y is a $C_{1-6}$ alkylene group, and each of $R^{4'}$ and $R^{5'}$ which may be same or different, is a $C_{1-6}$ alkyl group, provided that $R^{4'}$ and $R^{5'}$ may be the same or different from $R^4$ to $R^5$ in the above formula (IX). The strong base to be used for the above reaction, may, for example, be an organic lithium compound such as methyllithium, n-butyllithium, secbutyllithium, t-butyllithium, phenyllithium, lithiumdiisopropylamide or bistrimethylsilylllithiumamide, an alkali metal hydride such as sodium hydride or potassium hydride, or a Grignard compound such as methylmagnesium iodide, ethylmagnesium bromide or phenylmagnesium bromide. Such a strong base is used usually in an amount of 1 equivalent to the silanol compound of the above formula (XII). The reaction is preferably conducted at a relatively low temperature of from −70° C. to room temperature, since a side reaction can thereby a suppressed. Further, this reaction is preferably conducted in an organic solvent. As the solvent to be used here, hetrahydrofuran, benzene, toluene, n-hexane, chloroform or carbon tetrachloride is suitably employed. It is preferred to conduct this reaction in an atmosphere of inert gas such as argon or nitrogen.

On the other hand, a polyorganosiloxane having a halogenated alkyl group at its one terminal, of the above formula (IX) can readily be prepared also by reacting the cyclosiloxane compound of the above formula (XIII) and the chlorosilane compound of the above formula (XIV) in the same manner using an alkyllithium compound such as methyllithium, n-butyllithium, sec-butyllithium or t-butyllithium as an initiator, without using the silanol compound of the above formula (XII) in the above reaction. In this case, among the alkyl groups of $R^3$ to $R^5$ in the above formula (IX), two are the same as $R^4$ and $R^5$ in the formula (XIII) and one is the same as the alkyl group of the alkyllithium compound used here.

The silanol compound of the above formula (XII) may, for example, trimethylsilanol, triethylsilanol, tripropylsilanol, triisopropylsilanol, tributylsilanol, tripentylsilanol, trihexylsilanol, methydiethylsilanol, dimethylethylsilanol, dimethypropylsilanol, dimethyisopropylsilanol, dimethylbutylsilanol, dimethylisobutylsilanol, dimethyl-t-butylsilanol or dimethylhexylsilanol.

The cyclosiloxane compound of the above formula (XIII) includes, for example, the following compounds:

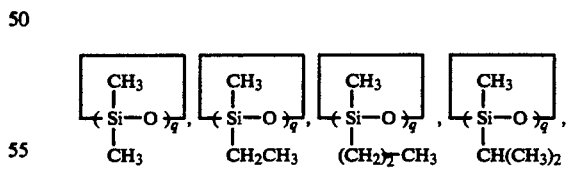

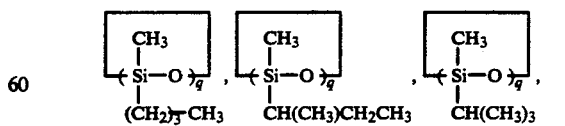

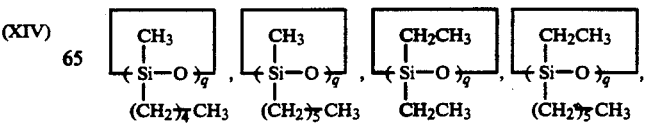

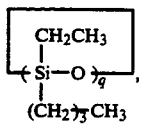

In the above formulas, q is an integer of from 3 to 6. Further, these cyclosiloxane compounds may be used in combination as a mixture of two or more.

The chlorosilane compound of the above formula (XIV) to be used as a terminating agent, may, for example, be chloromethyldimethylchlorosilane, 2-chloroethyldimethychlorosilane, 3-chloropropyldimethylchlorosilane, 4-chlorobutyldimethychlorosilane, 5-chloropentyldimethylchlorosilane, 6-chlorohexyldimethylchlorosilane, 3-bromopropyldimethychlorosilane, 4-bromobutyldimethylchlorosilane, iodomethyldimethylchlorosilane, 3-iodopropyldimethylchlorosilane, 4-iodobutyldimethylchlorosilane, 6-iodohexyldimethylchlorosilane or 3-chloropropyldiethylchlorosilane.

The polyorganosiloxane having a halogenated alkyl group at its one terminal, of the above formula (IX) to be produced by the above-described method, can simply be prepared by continuously adding the respective reaction reagents in the same container. Further, it is possible to control the degree of polymerization n of the polyorganosiloxane having a halogenated alkyl group at its one terminal, of the above formula (IX) and the polyorganosiloxane having a quaternary salt at its one terminal, of the above formula (I) of the present invention, by adjusting the amount of the cyclosiloxane compound of the above formula (XIII) to be used for the reaction. Further, in order to adjust this degree of polymerization n to a level of at least 3, it is necessary to use the cyclosiloxane compound of the above formula (XIII) in an amount of at least one equivalent relative to the initiator. However, in this case, the polyorganosiloxanes of the above formulas (I) and (II) will be mixtures of polyorganosiloxanes having different degrees of polymerization n, and the measured degrees of polymerization are represented by average values $\bar{n}$ (real number of at least 3).

The polyorganosiloxane having a quaternary salt at its one terminal, of the above formula (I) of the present invention is a compound which has both a quaternary salt as a polar group and a polyorganosiloxane chain as a hydrophobic group and thus has characteristics as a surfactant. Therefore, in addition to the use as an agent for promoting percutaneous absorption of a drug, the polyorganosiloxane of the present invention may be used as a cleaning agent, a germicide, an antiseptic, a cosmetic, etc. When it is used as an agent for promoting percutaneous absorption of a drug, its average degree of polymerization affects the promoting effects substantially, and in order to obtain high promoting effects, the average polymerization degree $\bar{n}$ is preferably within a range of from 3 to 100, more preferably within a range of from 3 to 50, although it varies depending upon the drug to be used.

The agent for promoting percutaneous absorption of a drug, consisting essentially of the polyorganosiloxane having a quaternary salt at its one terminal, of the above formula (I) of the present invention, may be used in an optional form such as tincture wherein it is dissolved in a solvent such as water or an alcohol together with a drug to be administered, or an ointment or cream wherein it is mixed together with the drug in an ointment or cream base, or a tape formulation prepared by incorporating it together with the drug in a polymer film or in an adhesive.

The content of the percutaneous absorption promoting agent of the present invention varies depending upon the mode of its use. However, it is usually within a range of from 1 to 50% by weight, preferably from 1 to 20% by weight. If the content is small, the absorption-promoting effects tend to be small. On the other hand, if it is large, side effects such as skin irritation tend to be remarkable, and the release of the drug may sometimes be suppressed.

The drug to be use in the present invention may be a drug for human or for animals. It includes, for example, antiphlongistic analgesics such as acetaminophenone, aspirin, methyl salicylate, choline salicylate, glycol salicylate, 1-menthol, camphor, mephenamic acid, furphenamic acid, indometacin, diclofenac, alclofenac, ibuprofen, ketoprofen, naproxen, pranoprofen, fenoprofen, fenprofen, flurbiprofen, indoprofen, fentiazac, tolmetin, suprofen, banzadac, bufexamac, piroxicam, phenylbutazone, oxyphenbutazone, clofezone, pentazocine and mepirizone; steroid antiphlogistics such as hydrocortisone, predonisolone, dexamethasone, triamcinolone acetonide, fluocinolone acetonide and fludrocortisone acetate; antihistamine or antiallergic agents such as chlorpheniramine, glycyrrhizic acid, diphenhydramine and periactin; local anesthetics such as benzocaine, procaine, dibucaine and lidocaine; antibacterial agents including tetracyclines such as chlorotetracycline, penicillins such as ampicillin, cephalosporins such as cephalothin, aminoglycosides such as kanamycin, macrolides such as erythromycin, chloramphenicol, iodide compounds, nitrofurantoin, nystatin, amphotericin, fradiomycin, sulfonamides, pyrrole nitoline, clotrimazole and nitrofurazone; antihypertensives such as clonidine, α-methyldopa, reserpine, syrosingopine, recinamin, cinnarizine, hydrazine and prazosin; depressor diuretics such as thephyline, trichlormethiazide, furosemide, tripamide, methyclothiazide, penfultizide, hydrocyazide, spironolactone and metolazone; cardiacs such as digitalis, ubidecarenon and dopamine; coronary vasodilators such as nitroglycerine, isosorbitol dinitrate, erythtosetetranitrate, pentaerythol tetranitrate, dipyridamole, dilazep, trapidil and trimethadizine; vasoconstrictors such as dihydroergotamine or dihydroergotoxine; β-blocker or antiarrhythmic agents such as pindol and propranolol; calcium antagonists such as diltiazem, nifedipine, nicardipine, verapamil, bencyclane and dilazep; antiepileptics such as nitroazepam, meprobamate and phenytoin; antivertigo agents such as isoprenaline, betahistine and scopolamine; tranquilizers such as diazepam, lorazepam, flunitrazepam and fluphenazine; hyposedatives such as phenobarbital, amobarbital and cyclobarbital; muscle relaxants such as triperizone, bacrophen, dantrolene sodium and cyclobenzapirin; drugs for automatic nerve such as atropine and levodopa; drugs for respiratory organ such as codeine, ephedrine, isoproterenol, dextromethorphan, olecypronaline, pratropium bromide and cromoglicic acid; hormone or antihormone agents such as corticortropin, oxytocin, vasopressin, testosterone, progesterone, estradiol, salivary gland hormone thyroid hormone, adrenal hormone, kallikrein, insulin and oxendolone; vitamins such as vitamins A, B, C, D, E and K and their derivatives, calciferols and mecobalamin; antitumor agents such as 5-fluorouracil and its derivatives, adriamycin, Krestin, picibanil, ancitabine and cytarabine; enzymes such as urokinase; Chinese medicines or crude drugs such as glycyrrhiza, aloe and lithospermum root; antiulcer agents such as allantoin, aldioxa and alcloxa; and others such as prostaglandins and antidiabetic agents. These drugs may be used in combination as a mixture of two or more, as the case requires.

The drug formulation containing the percutaneous absorption promoting agent of the present invention can be applied to the skin or the mucous membrane (oral cavity, nasal cavity, rectum or vagina) of various parts of a human body by coating a necessary amount depending upon the particular purpose. For example, for local treatment of an injury, skin ulcer, muscle pain or arthritis, it may be applied directly to the affected part or to a vicinity thereof. For systemic treatment of an internal organ, it is preferably applied to a site where the drug is readily absorbed (for example at a site where horny substance is not developed). Further, when it is used as a cosmetic, the drug formulation may be used as it is or as blended with a known cosmetic component for the purpose of e.g. cleaning or masking of the skin, preventing sun burn or skin roughening, or moisturizing the skin.

Now, the present invention will be described in further detail with reference to Reference Examples, Working Examples and Comparative Examples. However, it should be understood that the present invention is by no means restricted by such specific Examples. In the following reaction formulas and description, $D_3$ represents hexamethylcyclotrisiloxane, $F_3$ represents 1,3,5-trimethyl-1,3,5-tris(3,3,3-trifluoropropyl)cyclotrisiloxane, and n-BuLi represents n-butyllithium.

EXAMPLE 1

Polyorganosiloxane having a quaternary salt

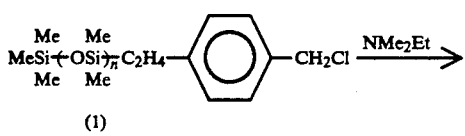

(1)

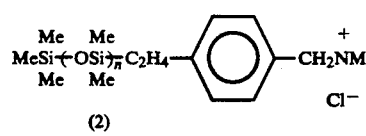

(2)

Silalane XN-1003 (5.0 g) manufactured by Chisso Corporation having a structure of the above chemical formula (1) and dimethylethylamine (0.8 g) were dissolved in 50 ml of tetrahydrofuran, and the solution was refluxed for about 15 hours. Then, the solvent and excess diethylamine were distilled off, and the residue was purified by silica gel column chromatography (developing solvent: ethyl acetate/methanol=50/50 vol%) to obtain 4.5 g of a polyorganosiloxane having a quaternary salt at its one terminal and having a structure of the chemical formula (2) as a colorless transparent viscous substance. The structure was confirmged by $^1$H-NMR and IR spectra. Further, from the $^1$H-NMR spectrum, the average degree of polymerization $\bar{n}$ in the above formula was found to be 15.5, and the bond represented by —$C_2H_4$— was found to be —CH(CH$_3$)— or —CH$_2$CH$_2$— and their ratio was found to be 21/79.

$^1$H-NMR, δ(CDCl$_3$, ppm): 0.10 (s, SiCH$_3$), 0.95 (m, Si—CH$_2$CH$_2$—Ph), 1.30 (d, Si—CH(CH$_3$)—Ph), 1.34 (t, N-CH$_2$CH$_3$), 2.15 (m, Si—CH$_3$)-Ph), 2.60 (m, Si—CH$_2$CH$_3$—Ph), 3.50-3.71 )m, N—$_3$, N—CH$_2$CH$_3$), 4,80 (s, Ph—CH$_2$—N), 7.22 (m, proton peak on the phenylene ring)

IR (cm$^{-1}$): 2960, 2900, 1720, 1610, 1440 (C—N), 1410, 1260 (Si—C), 1110-1000 (SiOSi), 800 (SiOSi), 680

EXAMPLE 2

Polyorganosiloxane having a quaternary salt

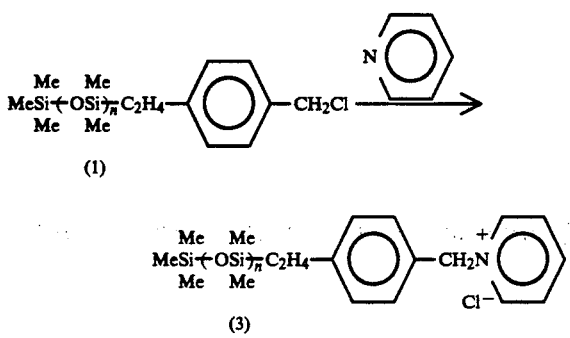

Using 0.9 g of pyridine instead of dimethylethylamine in Example 1, the reaction and purification were conducted in the same manner as in Example 1, to botain 3.2 g of a polyorganosiloxane having a quaternary salt at its one terminal and having a structure of the chemical formula (3), as a colorless transparent viscous substance. The structure was confirmged by $^1$H-NMR and IR spectra. Further, from the 1H-NMR spectrum, the average degree of polymerization $\bar{n}$ in the above formula was found to be 16.0 and the bond represented by —$C_2H_4$— was found to be —CH(CH$_3$)—or —CH$_2$CH$_2$— and their ratio was found to be 20/80.

$^1$H-NMR, δ(CDCl$_3$, ppm); 0.10 (s, Si—CH$_3$), 0.92 (m, Si—CH$_2$CH$_2$—Ph), 1.25 (d, Si—CH(CH$_3$)—Ph), 2.10 (m, Si—CH(CH$_3$)—Ph), 2.55 (m, Si—CH$_2$CH$_2$—Ph), 6.22 (s, Ph—CH$_2$—N), 7.20 (m, proton peak on the phenylene ring), 8.02 (m, proton peak on the pyridine ring), 8.38 (t, proton peak on the pyridine ring), 9.83 (d, proton peak on the pyridine ring)

IR(cm$^{-1}$): 2960, 2900, 1720, 1610, 1440, 1410 (C—N), 1260 (Si—C), 1110-1000 (SiOSi), 800 (SiOSi), 680

REFERENCE EXAMPLE 1

Polyorganosiloxane having a chloromethylphenyl group

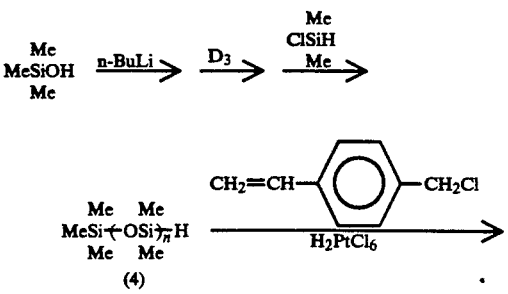

(4)

-continued

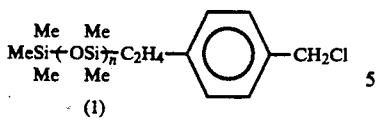

Trimethylsilanol (20.3 g) was dissolved in 200 ml of tetrahydrofuran, and a hexane solution of an equimolar amount of n-butyllithium was added thereto under an argon stream. After stirring the mixture for 10 minutes, a solution having $D_3$ (75.0 g) dissolved in 200 ml of tetrahydrofuran, was further added thereto. The mixture was stirred at room temperature for 20 hour. To this reaction solution, an excess amount of dimethylchlorosilane (about 4 mol equivalent) was added as a terminating agent to terminate the polymerization reaction. Then, the solvent was distilled off under reduced pressure, and the precipitated salt was filtered off, and the filtrate was heated under vacuum of at most 1 mmHg at 120° C. for two hours to remove unreacted cyclosiloxane and an excess terminating agent to obtain 93.8 g of a polyorganosiloxane having a Si-H bond at its one terminal and having a structure of the above chemical formula (4), as a colorless transparent viscous liquid.

The polyorganosiloxane (8.52 g) thus obtained and p-chloromethylstyrene (5.00 g, about 2 equivalent) were dissolved in 20 ml of toluene, and the solution was heated to 80° C. under an argon stream. Then, 100 μl of an isopropanol solution (0.1 mol/l) of chloroplatinic acid ($H_2PtCl_6 \cdot H_2O$) was added thereto, and the mixture was heated and stirred for about two hours. Then, the solvent was distilled off under reduced pressure, and the catalyst was filtered off by activated carbon. The filtrate was further heated under vacuum of at most 1 mmHg at 150° C. for two hours to remove unreacted p-chloromethylstyrene to obtain 9.10 g of a polyorganosiloxane having a chloromethylphenyl group at its one terminal and having a structure of the above chemical formula (1), as a colorless transparent oily substance. The structure was confirmed by $^1$H-NMR and IR spectra. Further, from the $^1$H-NMR spectrum, the average degree of polymerization $\bar{n}$ in the above formula was found to be 6.1, and the bond represented by $-C_2H_4-$ was found to be $-CH(CH_3)-$ or $-CH_2CH_2-$, and their ratio was found to be 31/69.

$^1$H-NMR, δ(CDCl3, ppm): 0.10 (s, Si—CH3), 0.93 (m, Si—CH2CH2—Ph), 1.40 (d, Si—CH(CH3)—Ph), 2.10 (m, Si—CH(CH3)—Ph), 2.71 (m, Si—CH2CH2—Ph), 4.61 (s, Ph—CH2Cl), 7.26 (m, proton peak on the phenylene ring) (cm$^{-1}$): 2980, 2920, 1415, 1260 (Si—C), 1110—1000 (SiOSi), 840, 800 (SiOSi), 680

EXAMPLE 3

Polyorqanosiloxane having a quaternary salt

Using 1.5 g of the polyorganosiloxane obtained in Reference Example 1 instead of Silaplane XN-1003 in Example 1, the reaction and purification were conducted in the same manner as in Example 1 to obtain 1.2 g of a polyorganosiloxane having a quaternary salt at its one terminal and having a structure of the chemical formula (1), as a colorless transparent viscous substance. The $^1$H-NMR and IR spectra of the product were the same as in Example 1. Further, from the $^1$H-NMR spectrum, the average degree of polymerization $\bar{n}$ in the above formula was found to be 7.2, and the bond represented by $-C_2H_4-$ was found to be $-CH(CH_3)-$ or $-CH_2CH_2-$, and their ratio was found to be 31/69.

REFERENCE EXAMPLE 2

Polyorganosiloxane having a chloromethylphenyl group

Using $D_3$ in an amount of 150 g in Reference Example 1, the polymerization reaction and purification were conducted in the same manner as in Reference Example 1 to obtain 155 g of a polyorganosiloxane having a Si-H bond at its one terminal and having a structure of the chemical formula (4). Further, 5.84 g of the product was subjected to the reaction with p-chloromethylstyrene and purification in the same manner to obtain 6.20 g of a polyorganosiloxane having a chloromethylphenyl group at its one terminal and having a structure of the chemical formula (1), as a colorless transparent oily substance. The $^1$H-NMR and IR spectra of the product were the same as in Reference Example 1. Further, from the $^1$H-NMR spectrum, the average degree of polymerization $\bar{n}$ in the formula (1) was found to be 12.1, and the bond represented by $-C_2H_4-$ was found to be $-CH(CH_3)-$ or $-CH_2CH_2-$, and their ratio was found to be 34/66.

EXAMPLE 4

Polyorganosiloxane having a quaternary salt

Using 1.5 g of the polyorganosiloxane obtained in Reference Example 2 instead of Silaplane XN-1003 in Example 1, the reaction and purification were conducted in the same manner as in Example 1 to obtain 1.2 g of a polyorganosiloxane having a quaternary salt at its one terminal and having a structure of the chemical formula (1), as a colorless transparent viscous substance. The $^1$H-NMR and IR spectra of the product were the same as in Example 1. Further, from the 1H-NMR spectrum, the average degree of polymerization $\bar{n}$ in the above formula was found to be 13.5, and the bond represented by $-C_2H_4-$ was found to be $-CH(CH_3)-$ or $-CH_2CH_2-$, and their ratio was found to be 35/65.

REFERENCE EXAMPLE 3

Polyorganosiloxane having a chloromethylphenyl group

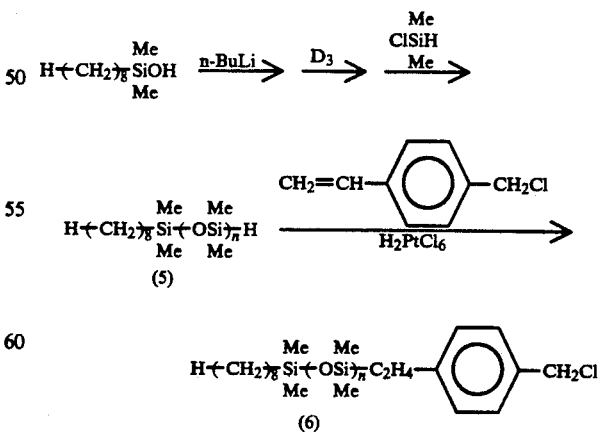

In Reference Example 1, 4.25 g of dimethyloctylsilanol was used instead of trimethylsilanol and the amount of $D_3$ was changed to 15.1 g, and the reaction and purification were conducted in the same manner as Reference Example 1 to obtain 15.5 g of a polyorganosiloxne having a Si—H bond at its one terminal and having a structure of the chemical formula (5). Further, 3.13 g of the product was subjected to the reaction with p-chloromethylstyrene and the purification in the same manner to obtain 3.15 g of a polyorganosiloxane having a chloromethylphenyl group at its one terminal and having a structure of the chemical formula (6), as a colorless oily substance. The structure was confirmed by $^1$H-NMR and IR spectra. Further, from the $^1$H-NMR spectrum, the average degree of polymerization $\bar{n}$ in the above formula was found to be 13.5, and the bond represented by —C$_2$H$_4$— was found to be —CH(CH$_3$)— or —CH$_2$CH$_2$—, and their ratio was found to be 35/65. $^1$H-NMR, δ, (CDCl$_3$): 0110 (s, Si—CH$_3$), 0.55 (m, Si—CH$_2$(CH$_2$)$_6$)CH$_3$), 0.82-1.1 (m, Si—CH$_2$CH$_2$—Ph, Si—CH$_2$(CH$_2$)$_6$CH$_3$), 1.20-1.50 (m, Si—CH(CH$_2$)—Ph, Si—CH$_2$(CH$_2$)$_6$CH$_3$), 2.11 (m, Si—CH(CH$_3$)—Ph), 2.75 (m, Si—CH$_2$CH$_2$—Ph), 4.59 (s, —CH$_2$Cl), 7.26 (m, proton peak on the phenylene ring)

IR (cm$^{-1}$): 2980, 2940, 2890, 2860, 1415, 1260 (Si—C), 1110-1000 (SiOSi), 840, 800 (SiOSi), 700, 680

EXAMPLE 5

Polyorganosiloxane having a quaternary salt

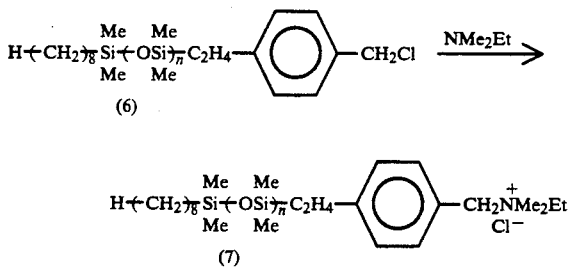

Using 1.5 g of the polyorganosiloxane obtained in Reference Example 3 instead of Silaplane XN-1003 in Example 1, the reaction and purification were conducted in the same manner as in Example 1 to obtain 1.0 g of a polyorganosiloxane having a quaternary salt at its one terminal and having a structure of the chemical formula (7), as a colorless transparent viscous substance. The structure was confirmed by $^1$H-NMR and IR spectra. Further, from the $^1$H-NMR spectrum, the average degree of polymerization $\bar{n}$ in the above formula was found to be 14.0, and the bond represented by —C$_2$H$_4$— was found to be —CH(CH$_3$)— or —CH$_2$CH$_2$—, and their ratio was found to be 33/67.

$^1$H—NMR, δ, (CDCl$_3$) 0.10 (s, Si—CH$_3$), 0.56 (m, Si—CH$_2$(CH$_2$)$_6$CH$_3$), 0.75-1.05 (m, Si—CH$_2$CH$_2$—Ph, Si—CH$_2$(CH$_2$)$_6$CH$_3$), 1.15-1.45 (m, Si—CH(CH$_3$)—Ph, Si—CH$_2$(CH$_2$)$_6$CH$_3$, N—CH$_2$CH$_3$), 2.22 (m, Si—CH(CH$_3$)—Ph), 2.60 (m, Si—CH$_2$CH$_2$—Ph), 3,42-3.75 (m, N-CH$_3$, N—CH$_2$CH$_3$), 4.88 (s, Ph—CH$_2$—N), 7.30 (m, proton peak on the phenylene ring)

IR (cm$^{-1}$): 2960, 2930, 3890, 2860, 1610, 1440 (C—N), 1410, 1255 (Si—C), 1110-1000 (SiOSi), 800 (SiOSi), 680

EXAMPLE 6

Polyorganosiloxane having a quaternary salt

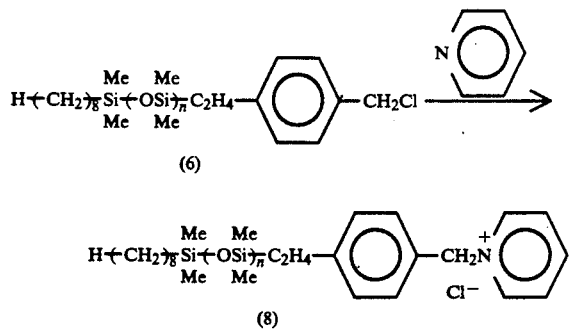

Using 1.0 g of the polyorganosiloxane obtained in Reference Example 3 instead of Silaplane XN-1003 and 0.5 g of pyridine instead of dimethylethylamine in Example 1, the reaction and purification were conducted in the same manner as in Example 1 to obtain 0.8 g of a polyorganosiloxane having a quaternary salt at its one terminal and having a structure of the chemical formula (8), as a colorless transparent viscous substance. The structure was confirmed by $^1$H-NMR and IR spectra. Further, from the $^1$H-NMR spectrum, the average degree of polymerization $\bar{n}$ in the above formula was found to be 14.5, and the bond represented by —C$_2$H$_4$— was found to be —CH(CH$_3$)—or —CH$_2$CH$_2$—, and their ratio was found to be 35/65. $^1$H-NMR, δ, (CDCl$_3$) 0.10 (s, Si—CH$_2$), 0.56 (m, Si—CH$_2$(CH$_2$)$_6$CH$_3$), 0.80-1.10 (m, Si—CH$_2$(CH$_2$)Ph, Si—CH$_2$CH$_2$(CH$_2$)$_6$CH$_3$), 1.20-1.51 (m, Si—CH(CH3)-Ph, Si—CH$_2$ (CH$_2$)$_6$CH$_3$), 2.12 (m, Si—CH(CH$_3$)—Ph), 2.55 (m, Si—CH$_2$CH$_2$—Ph), 6.22 (s, Ph-CH$_2$—N), 7.20 (m, proton peak on the phenylene ring), 8.02 (m, proton peak on the pyridine ring), 8.38 (t, proton peak of the pyridine ring), 9.53 (d, proton peak on the pyridine ring) IR (cm$^{-1}$) 2960, 2890, 2860, 1720, 1610, 1440, 1410 (C-N), 1260 (Si-C), 1110-1000 (SiOSi), 800 (SiOSi), 680

REFERENCE EXAMPLE 4

Polyorganosiloxane having a chloromethylphenyl group

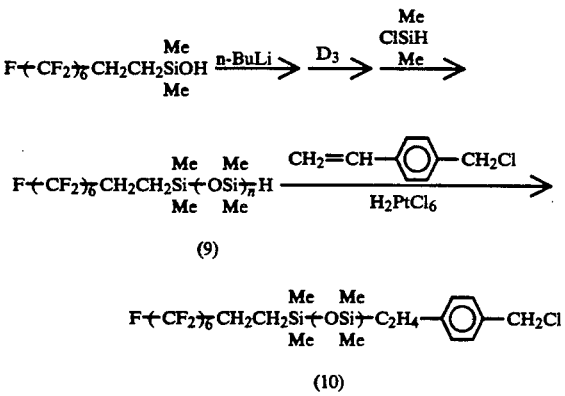

In Reference Example 1, 8.00 g of dimethyl-1H,1H,2H,2-tridecafluorooctylsilanol was used instead trimethylsilanol and the amount of D$_3$ was changed to 8.44 g, and the polymerization reaction and purification were conducted in the same manner as in Reference Example 1 to obtain 12.1 g of a polyorganosiloxane having a Si—H bond at its one terminal and having a structure of the chemical formula (9). Then, 5.09 g of the product was subjected to the reaction with p-chloromethylstyrene and the purification in the same manner to obtain 5.11 g of a polyorganosiloxane having a chloromethylphenyl group at its one terminal and having a structure of the chemical formula (10), as a colorless transparent oily substance. The structure was confirmed by $^1$H-NMR and IR spectra. Further, from the $^1$H-NMR spectrum, the average degree of polymerization $\bar{n}$ in the above formula was found to be 9.1, and the bond represented by —$C_2H_4$— was found to be —$CH(CH_3)$— or —$CH_2CH_2$—, and their ratio was found to be 38/62. $^1$H-NMR, δ, ($CDCl_3$): 0.10 (s, Si—$CH_3$), 0.75–1.05 (m, Si—$CH_2CH_2$—Ph, Si—$CH_2CH_2(CF_2)_6F$), 1.44 (d, Si—$CH(CH_3)$—Ph), 1.95–2.36 (m, Si—$CH(CH_3)$—Ph, Si—$CH_2CH_2(CF_2)_6F$), 2.76 (m, Si—$CH_2CH_2$—Ph), 4.59 (s, —$CH_2Cl$), 7.26 (m, proton peak of the phenylene ring)

IR($cm^{-1}$): 2980, 2920, 1415, 1260 (Si—C), 1240, 1210 (C-F), 1145, 1110–1000 (SiOSi), 900, 840, 800 (SiOSi), 705

EXAMPLE 7

Polyorganosiloxane having a quaternary salt

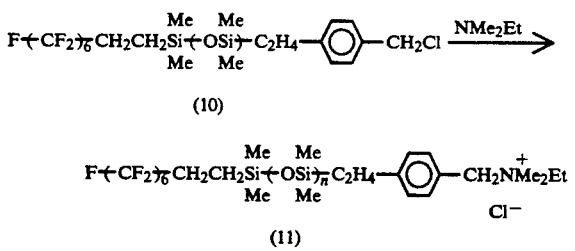

Using 1.5 g of the polyorganosiloxane obtained in Reference Example 4 instead of Silaplane XN-1003 in Example 1, the reaction and purification were conducted in the same manner as in Example 1 to obtain 1.2 g of a polyorganosiloxane having a quaternary salt at its one terminal and having a structure of the chemical formula (11), as a colorless transparent viscous substance. The structure was confirmed by $^1$H-NMR and IR spectra. Further, from the $^1$H-NMR spectrum, the average degree of polymerization n in the above formula was found to be 9.5, and the bond represented by —$C_2H_4$—was found to be —$CH(CH_3)$— or —$CH_2CH_2$—, and their ratio was found to be 36/64. $^1$H-NMR, δ, ($CDCl_3$): 0.10 (s, Si—$CH_3$), 0.55–0.92 (m, Si—$CH_2C$H_2—Ph, Si—$CH_2CH_2(CF_2)_6F$), 1.00–1.48 (m, Si—$CH(CH_3)$—Ph), 1.60–2.32 (m, Si—$CH(CH_3)$—Ph, Si—$CH_2CH_2(CF_2)_6F$), 2.58 (m, Si—$CH_2CH_2$—Ph), 3.34–3.78 (m, N—$CH_3$, N—$CH_2CH_3$), 4.85 (s, Ph—$CH_2$—N), 7.30 (m, proton peak of the phenylene ring)

IR ($cm^{-1}$): 2950, 2900, 1610, 1440 (C—N), 1410, 1260 (Si-C), 1210 (C-F), 1110–1000 (SiOSi), 900, 800 (SiOSi), 700

EXAMPLE 8

Polyorganosiloxane having a quaternary salt

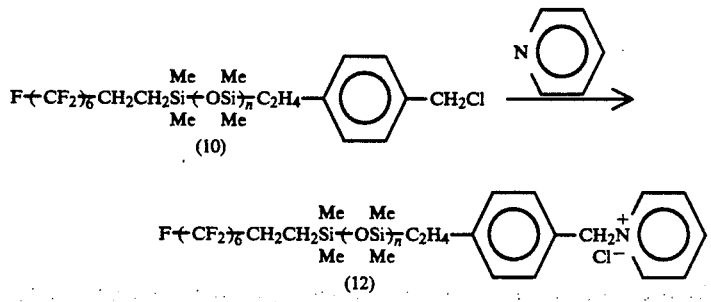

Using 1.5 g of the polyorganosiloxane obtained in Reference Example 4 instead of Silaplane XN-1003 and 0.5 of pyridine instead of dimethylethylamine in Example 1, the reaction and purification were conducted in the same manner as in Example 1 to obtain 1.1 g of a polyorganosiloxane having a quaternary salt at its one terminal and having a structure of the chemical formula (12), as a colorless transparent viscous substance. The structure was confirmed by $^1$H-NMR and IR spectra. Further, from the $^1$H-NMR spectrum, the average degree of polymerization $\bar{n}$ in the above formula was found to be 9.5, and the bond represented by —$C_2H_4$—was found to be —$CH(CH_3)$— or —$CH_2C$H_2—, and their ratio was found to be 35/65.

$^1$H-NMR, δ, ($CDCl_3$): 0.10 (s, Si—$CH_3$), 0.70–1.05 (m, Si—$CH_2CH_2$—Ph, Si—$CH_2CH_2(CF_2)_6F$), 1.42 (d, Si—$CH(CH_3)$—Ph), 1.92–2.32 (m, Si—$CH(CH_3)$—Ph, Si—$CH_2CH_2(CF_2)_6F$), 2.58 (m, Si—$CH_2CH_2$—Ph), 6.25 (s, Ph—$CH_2$—N), 7.20 (m, proton peak of the phenylene ring), 8.02 (m, proton peak on the pyridine ring), 8.38 (t, proton peak on the pyridine ring), 9.53 (d, proton peak on the pyridine ring)

IR ($cm^{-1}$): 2960, 2900, 1720, 1610, 1440, 1410 (C—N), 1260 (Si—C), 1240, 1210 (C—F), 1145, 1110–1000 (SiOSi), 900, 800 (SiOSi), 690

REFERENCE EXAMPLE 5

Polyorganosiloxane having a chloromethylphenyl group

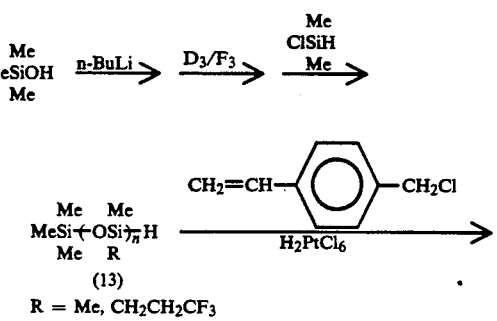

R = Me, $CH_2CH_2CF_3$

-continued

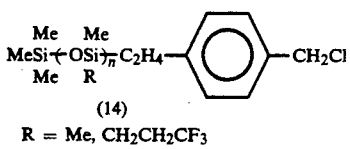

(14)

R = Me, CH$_2$CH$_2$CF$_3$

In Reference Example 1, the amount of trimethylsilanol was changed to 4.00 g and a D$_3$/F$_3$ mixture (9.90 g/16.8 g) was used instead of D$_3$, and the polymerization reaction and purification were conducted in the same manner as in Reference Example 1 to obtain 29.8 g of a polyorganosiloxane having a Si—H bond at its one terminal and having a structure of the chemical formula (13). Further, 5.24 g of the product was subjected to the reaction with p chloromethylstyrene and the purification in the same manner to obtain 5.20 g of a polyorganosiloxane having a chloromethylphenyl group at its one terminal and having a structure of the chemical formula (14), as a colorless transparent oily substance. The structure was confirmed by $^1$H-NMH and IR spectra. Further, from the $^1$H-NMR spectrum, the substituent for R in the above formula was found to be a methyl group or a 3,3,3-trifluoropropyl group and their molar ratio was found to be 58/42, and the average degree of polymerization $\bar{n}$ was found to be 5.6, and the bond represented by —C$_2$H$_4$—was found to be —CH(CH$_3$)—or —CH$_2$CH$_2$, and their ratio was found to be 43/57.

$^1$H-NMR, δ, (CDCl$_3$): 0.10 (s, Si—CH$_3$), 0.60–0.98 (m, Si—CH$_2$CH$_2$—Ph, Si—CH$_2$CH$_2$CF$_3$), 1.38 (d, Si—CH(CH$_3$)—Ph), 1.85–2.25 (m, Si—CH(CH$_3$)—Ph, Si—CH$_2$CH$_2$CF$_3$), 2.69 (m, Si—CH$_2$CH$_2$—Ph), 4.58 (s, —CH$_2$Cl), 7.26 (m, proton peak of the phenylene ring)

IR (cm$^{-1}$): 2980, 2920, 1445, 1415, 1370, 1318, 1260 (Si— C), 1210 (C-F), 1130, 1110–1000 (SiOSi), 900, 840, 800 (SiOSi), 680

EXAMPLE 9

Polyorganosiloxane having a quaternary salt

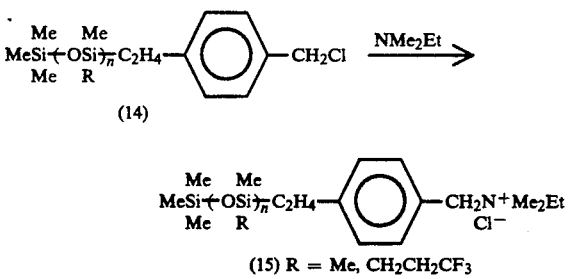

(15) R = Me, CH$_2$CH$_2$CF$_3$

Using 1.5 g of the polyorganosiloxane obtained in Reference Example 5 instead of Silaplane XN-1003 in Example 1, the reaction and purification were conducted in the same manner as in Example 1 to obtain 1.1 g of a polyorganosiloxane having a quaternary salt at its one terminal and having a structure of the chemical formula (15), as a colorless transparent viscous substance. The structure was confirmed by $^1$H-NMR and IR spectra. Further, from the $^1$H-NMR spectrum, the substituent for R in the above formula was found to be methyl group or a 3,3,3-trifluoropropyl group and their molar ratio was found to be 67/10, the average degree of polymerization $\bar{n}$ in the above formula was found to be 6.5, and the bond represented by —C$_2$H$_4$— was found to be —CH(CH$_3$)—or — CH$_2$CH$_2$—, and their ratio was found to be 43/57.

$^1$H-NMR, δ, (CDCl$_3$) 0.10 (s, Si—CH$_3$), 0.55–0.98 (m, Si—CH$_2$CH$_2$—Ph, Si—CH$_2$CH$_2$CF$_3$), 1.05–1.50 (m, Si—CH(CH$_3$)—Ph, N—CH$_2$CH$_3$), 1.65–2.22 (m, Si—CH(CH$_3$)—Ph, Si—CH$_2$CH$_2$CF$_3$), 2.68 (m, Si—CH$_2$CH$_2$—Ph), 3.32–3.80 (m, N—CH$_2$, N—CH$_2$CH$_3$), 4.85 (s, Ph—CH$_2$—N), 7.29 (m, proton peak of the phenylene ring)

IR (cm$^{-1}$): 2950, 2900, 1610, 1440 (C-N), 1410, 1260 (Si—C), 1210 (C-F), 1110–1000 (SiOSi), 900, 800 (SiOSi), 700

EXAMPLES 10 to 18

Test for penetration of a drug through the skin

The skin pealed from the abdominal part of a rabbit was held between two chambers of a two-chamber diffusion cell (effective cross-sectional area: 0.95 cm$^2$). To the donor chamber, 2 ml of a 50% ethyl alcohol aqueous solution containing 20 mg (1 wt%) of antiphlogistic indometacin and the polyorganosiloxane having a quaternary salt at its one terminal (percutaneous absorption promoting agent) (2 wt%) obtained in one of Examples 1 to 9, was introduced, and to the receptor chamber, 2 l of a phosphate buffer solution adjusted to pH =7.4 was introduced. The entire cell was immersed in a constant temperature tank of 37° C. The two chambers were maintained under stirring, and upon expiration of 6 hours and 12 hours, a sample was taken from the receptor chamber, and the permeated indometacin was quantitatively analyzed by high performance liquid chromatography. The results of the penetration test obtained by using the polyorganosiloxanes having a quaternary salt at one terminal, obtained in Examples 1 to 9, as percutaneous absorption-promoting agents, respectively, are shown in Table 1. In Table 1, Comparative Example is the test conducted in the same manner except that no polyorganosiloxane was added. As is evident from Table 1, all of the polyorganosiloxanes having a quaternary salt at one terminal exhibit excellent percutaneous absorption-promoting effects. Further, the surface of the skin pealed from the abdominal part of the rabbit on the donor chamber site was inspected after the test, whereby no color change was observed in each case, and it was confirmed that no change took place from the state before the test.

TABLE 1

| Examples No | Polyorganosiloxane used as a percutaneous absorption-promoting agent | Cumulative penetrated amount after 6 hours (mg) | Cumulating penetrated amount after 12 hours (mg) |
|---|---|---|---|
| 10 | Example 1 | 0.048 ± 0.001 | 0.137 ± 0.025 |
| 11 | Example 2 | 0.033 ± 0.003 | 0.096 ± 0.010 |
| 12 | Example 3 | 0.057 ± 0.004 | 0.169 ± 0.015 |
| 13 | Example 4 | 0.052 ± 0.006 | 0.187 ± 0.018 |
| 14 | Example 5 | 0.049 ± 0.008 | 0.136 ± 0.012 |
| 15 | Example 6 | 0.096 ± 0.037 | 0.288 ± 0.081 |
| 16 | Example 7 | 0.032 ± 0.001 | 0.098 ± 0.021 |
| 17 | Example 8 | 0.030 ± 0.006 | 0.100 ± 0.022 |
| 18 | Example 9 | 0.025 ± 0.004 | 0.078 ± 0.010 |
| Comparative Example 1 | Nil | 0.012 ± 0.001 | 0.033 ± 0.003 |

Results of the test for measuring the absorption and penetration of indometacin by means of the rabbit skin

*The penetrated amount is an average value of the three tests conducted with respect to the skins of three rabbits.

REFERENCE EXAMPLES 6 TO 8

Polyorganosiloxane having a chloropropyl group at its one terminal

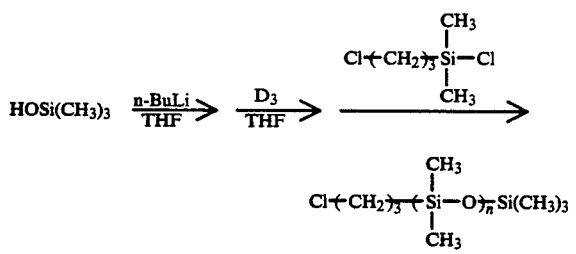

Trimethylsilanol in an amount as identified in Table 2 was dissolved in 100 ml of tetrahydrofuran, and under an argon gas atmosphere, a hexane solution (1.6 mol/l) of n-butyllithium was added in an equimolar amount to trimethylsilanol at 0° C. The mixture was stirred for about one hour. To the solution, a solution having hexamethylcyclotrisiloxane (D3) in an amount as identified in Table 2 dissolved in 180 ml of tetrahydrofuran, was added, and the mixture was further stirred at room temperature for 12 hours. Then, 3-chloropropyldimethylchlorosilane was added in an amount as identified in Table 2 to terminate the reaction. After distilling the solvent off, the formed salt was filtered off, and the filtrate was heated and stirred under reduced pressure at 120° C. for two hours to obtain a colorless transparent viscous oil. From the following results of the $^1$H-NMR and IR spectra, the product was found to be a polydimethylsiloxane of the above identified structure having a 3-chloropropyl group at one terminal and a trimethylsilyl group at the other terminal. In the above structure, the average degree of polymerization $\bar{n}$ of the polydimethylsiloxane chain was obtained from the integral ratio of the protone peak of the methyl group on the silyl group to the protone peak of the 3-chloropropyl group in the 1H-NMR spectrum.

The results are shown in Table 2.

$^1$H-NMR spectrum, δ(CDCl₃, ppm): 0.05 (s, proton peak of the methyl group on silicon), 0.49–0.69 (m,

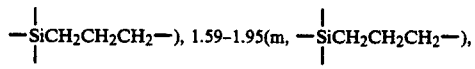

3.49(t, —CH₂Cl)

IR spectrum (cm⁻¹): 2990, 1420, 1265, 1110, 1030, 805

EXAMPLES 19 TO 21

Synthesis of polyorganosiloxane having a pyridinium salt at its one terminal

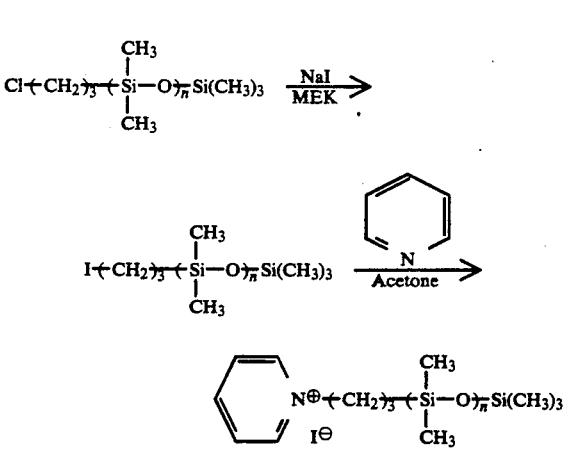

The polydimethylsiloxane having a 3-chloropropyl group at its one terminal obtained in one of Reference Examples 6 to 8 and sodium iodide were dissolved in 150 ml of ethyl methyl ketone in the respective amounts as identified in Table 3, and the solution was stirred under heating at 90° C. overnight. After completion of the reaction, the solid was filtered off, and the filtrate was washed with water and extracted with ethyl ether. Then, the solvent was distilled off. As a result, a mixture of polydimethylsiloxanes having a 3-chloropropyl group and a 3-iodopropyl group at their one terminals, respectively, was obtained as a colorless transparent viscous liquid. The $^1$H-NMR spectrum of this mixture is shown below.

$^1$H-NMR spectrum, δ(CDCl₃, ppm): 0.07 (s, proton peak of the methyl group on silicon), 0.54–0.73 (m,

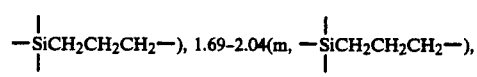

3.19(t, —CH₂I)

Then, 10 g of this polydimethylsiloxane mixture and pyridine in an amount as identified in Table 3 were dissolved in 25 ml of acetone, and the solution was refluxed for 24 hours. After completion of the reaction, the solvent and unreacted pyridine were distilled off, and the residue was purified by silica gel column chromatography to obtain a brown solid. From the following results of the $^1$H-NMR and IR spectra, the product in each Example was found to be a polydimethylsiloxane of the above structure having a pyridinium salt at one terminal and a trimethylsilyl group at the other terminal. In the above structure, the average degree of

TABLE 2

| Reference Examples No. | Amount of trimethylsilanol g (mmol) | Amount of D₃ g (mmol) | Amount of 3-chloropropyldimethyl chlorosilane ml (mmol) | Amount of the obtained polysiloxane g | Average degree of polymerization $\bar{n}$ |
|---|---|---|---|---|---|
| 6 | 6.08 (67.4) | 30.0 (135) | 22.2 (135) | 25.8 | 7.3 |
| 7 | 4.05 (45.0) | 30.0 (135) | 22.2 (135) | 28.0 | 10.5 |
| 8 | 2.43 (27.0) | 30.0 (135) | 9.23 (53.9) | 26.4 | 15.8 | polymerization n̄ of the polydimethylsiloxane chain, was obtained from the integral ratio of the protone peak of the methyl group on the silyl group to the protone peak of the pyridinium group at one terminal in the ¹H-NMR spectrum. The results are shown in Table 3. In the polydimethylsiloxane mixture used as the starting material in this reaction, the polydimethylsiloxane having a 3-chloropropyl group at one terminal, was recovered as an unreacted product.

¹H-NMR spectrum, δ(CDCl₃, ppm): 0.05 (s, proton peak of the methyl group on silicon), 0.29–0.71

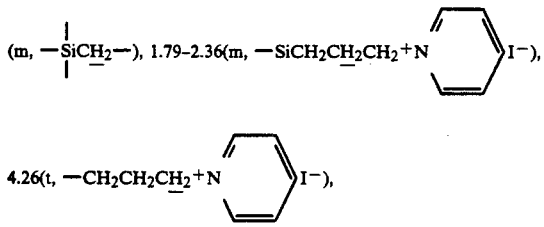

(m, —SiCH₂—), 1.79–2.36(m, —SiCH₂CH₂CH₂⁺N⟨⟩I⁻), 4.26(t, —CH₂CH₂CH₂⁺N⟨⟩I⁻), 8.06–8.22, 8.47–8.66, 9.26 (m, m, d, each being a proton peak on the pyridine ring)

anes having a 3-chloropropyl group and a 3-idodopropyl group at their one terminals, respectively, The ¹H-NMR spectrum of this mixture was the same as in Examples 19 to 21.

Then, 10 g of this polydimethylsiloxane mixture and 2.60 g (35.5 mmol) of dimethylethylamine were dissolved in 25 ml of acetone, and the solution was refluxed for 24 hours. After completion of the reaction, the solvent and unreacted dimethylethylamine were distilled off, and the residue was purified by silica gel column chromatography to obtain 5.4 g of a yellow solid. From the following results of the ¹H-NMR and IR spectra, the product in each Example was found to be a polydimethylsiloxane of the above structure having an ammonium salt at one terminal and a trimethylsilyl group at the other terminal. In the above structure, the average degree of polymerization n̄ of the polydimethylsiloxane chain was 7.1 as obtained from the integral ratio of the protone peak of the methyl group on the silyl group to the protone peak of the dimethylethyl ammonium group at one terminal in the ¹H-NMR spectrum. In the polydimethylsiloxane mixture used as the starting material in this reaction, the polydimethylsiloxane having a 3-chloropropyl group at one terminal, was

TABLE 3

| Examples No. | Polysiloxane used as starting material and its amount g (mmol) | Amount of NaI g (mmol) | Amount of pyridine ml (mmol) | Amount of the obtained polysiloxane g | Average degree of polymerization n |
|---|---|---|---|---|---|
| 19 | Reference Example 6, 10.0 (14.4) | 7.29 (48.7) | 1.20 (38.6) | 3.5 | 6.6 |
| 20 | Reference Example 7, 10.0 (10.8) | 5.36 (35.8) | 1.70 (56.7) | 5.1 | 9.8 |
| 21 | Reference Example 8, 10.0 (7.56) | 3.73 (24.9) | 1.20 (38.6) | 4.6 | 14.2 |

EXAMPLE 22

Synthesis of polyorqanosiloxane having an ammonium salt at its one terminal

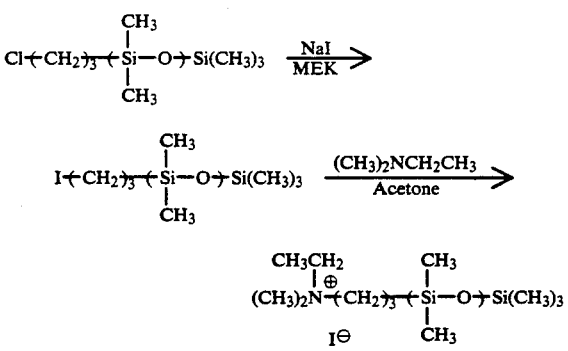

10.0 g (14.4 mmol) of the polydimethylsiloxane having a 3-chloropropyl group at its one terminal obtained in Reference Example 6 and 7.30 g (48.7 mmol) of sodium iodide were dissolved in 150 ml of ethyl methyl ketone, and the solution was stirred under heating at 90° C. overnight. After completion of the reaction, the solid was filtered off, and the filtrate was washed with water and extracted with ethyl ether. Then, the solvent was distilled off. As a result, a mixture of polydimethylsiloxrecovered as an unreacted product.

¹H-NMR spectrum, δ(CDCl₃, ppm): 0.05 (s, protone peak of the methyl group on silicon), 0.40–0.72

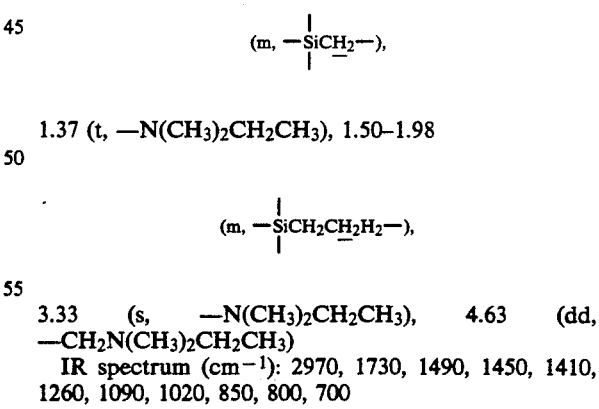

(m, —SiCH₂—), 1.37 (t, —N(CH₃)₂CH₂CH₃), 1.50–1.98

(m, —SiCH₂CH₂H₂—), 3.33 (s, —N(CH₃)₂CH₂CH₃), 4.63 (dd, —CH₂N(CH₃)₂CH₂CH₃)

IR spectrum (cm⁻¹): 2970, 1730, 1490, 1450, 1410, 1260, 1090, 1020, 850, 800, 700

EXAMPLES 23 TO 26

The test for measuring the penetration of indometacin through the skin of the abdominal part of a rabbit, was conducted in the same manner as in Examples 10 to 18 with respect to the polyorganosiloxanes obtained in Examples 6 to 9. The results of the penetration test are shown in Table 4. Further, in Comparative Example 2, the test was conducted in the same manner except that no polydimethylsiloxane was added, and the results are shown also in Table 4. As is evident from Table 4, polydimethylsiloxanes having a quaternary salt at one terminal all exhibit excellent percutaneous absorption promoting effects.

TABLE 4

| Examples No. | Percutaneous absorption-promoting agent used | Amount of indometacin (mg) | Penetrated amount* after 6 hours (mg) | Penetrated amount* after 12 hours (mg) |
| --- | --- | --- | --- | --- |
| 23 | Example 6 | 20 | 0.117 ± 0.010 | 0.260 ± 0.017 |
| 24 | Example 7 | 20 | 0.140 ± 0.001 | 0.302 ± 0.007 |
| 25 | Example 8 | 20 | 0.096 ± 0.012 | 0.247 ± 0.011 |
| 26 | Example 9 | 20 | 0.055 ± 0.003 | 0.167 ± 0.009 |
| Comparative Example 2 | Nil | 20 | 0.012 ± 0.001 | 0.031 ± 0.003 |

*The penetrated amount is an average value of the four tests conducted with respect to the skins of four rabbits.

We claim:

1. A polyorganosiloxane having a quaternary salt at its one terminal, of the following formula (I):

$$R^2-\underset{\underset{R^3}{|}}{\overset{\overset{R^1}{|}}{Si}}-(OSi)_{\overline{n}}-\underset{\underset{R^5}{|}}{\overset{\overset{R^4}{|}}{Y}}-A^+ \quad X^- \quad (I)$$

wherein A is

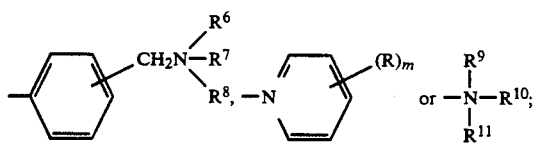

$X^-$ is a counter anion in the quaternary salt; each of $R^1$ to $R^5$ which may be the same or different, is an alkyl group, a substituted alkyl group or a phenyl group; Y is a $C_{1-6}$ linear or branched bivalent alkylene or oxyalkylene group; and n is an integer of at least 1, provided that when n is 2 or more, each of $R^4$ and $R^5$ may be the same or different, wherein each of $R^6$ to $R^8$ which may be the same or different, is an alkyl group, a substituted alkyl group or a phenyl group, or $R^6$ to $R^8$ together form a ring and/or an unsaturated bond; R is a $C_{1-6}$ alkyl group or a phenyl group; m is an integer of from 0 to 3, provided that when is 2 or 3, each R may be the same or different; and each of $R^9$ to $R^{11}$ which may be the same or different, is a phenyl group, a benzyl group or a $C_{1-6}$ alkyl group.

2. The polyorganosiloxane according to claim 1, wherein A is

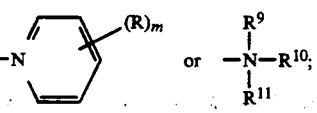

X is a halogen atom; each of $R^1$ to $R^5$ which may be the same or different, is a $C_{1-6}$ alkyl group; Y is a $C_{1-6}$ linear or branched bivalent alkylene group; n is an integer of at least 3, and each of $R^4$ and $R^5$ may be the same or different; and R, m, $R^9$ $R^{10}$ and $R^{11}$ are as defined in claim 1.

3. The polyorganosiloxane according to claim 1, wherein

A is 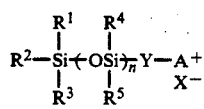

Y is a $C_{2-6}$ linear or branched bivalent alkylene or oxyalkylene group; and $X^-$, $R^1$ to $R^8$ and n are as defined in claim 1.

4. The polyorganosiloxane according to claim 1, wherein $X^-$ is a halogen ion, a hydroxyl ion, a carbonate ion, a sulfate ion, a hydrogensulfate ion, a sulfite ion, a nitrate ion, a phosphate ion, a carboxylic acid ion, a sulfonic acid ion or a phosphonic acid ion.

* * * * *